United States Patent [19]

Payne et al.

[11] Patent Number: 5,589,382
[45] Date of Patent: Dec. 31, 1996

[54] BACILLUS THURINGIENSIS GENES ENCODING NEMATODE-ACTIVE TOXINS

[75] Inventors: Jewel Payne, Davis; Kenneth E. Narva; Jenny Fu, both of San Diego, all of Calif.

[73] Assignee: Mycogen Corporation, San Diego, Calif.

[21] Appl. No.: 485,568

[22] Filed: Jun. 7, 1995

Related U.S. Application Data

[63] Continuation-in-part of Ser. No. 310,197, Sep. 21, 1994, and Ser. No. 357,698, Dec. 16, 1994, which is a division of Ser. No. 176,403, Dec. 30, 1993, abandoned, which is a continuation-in-part of Ser. No. 999,053, Dec. 31, 1992, abandoned, said Ser. No. 310,197, is a division of Ser. No. 92,155, Jul. 15, 1993, Pat. No. 5,350,577, which is a division of Ser. No. 918,345, Jul. 21, 1992, Pat. No. 5,270,448, which is a division of Ser. No. 558,738, Jul. 27, 1990, Pat. No. 5,151,363.

[51] Int. Cl.$^6$ ............................. C12N 1/20; A01N 63/00
[52] U.S. Cl. .................................. 435/252.5; 435/252.31; 435/832; 424/93.461; 424/93.2
[58] Field of Search ........................... 435/252.3, 252.31, 435/252.33, 252.34, 252.35, 252.5, 832; 424/93.2, 93.461

[56] References Cited

U.S. PATENT DOCUMENTS

| | | | |
|---|---|---|---|
| 4,781,922 | 11/1988 | Bone . | |
| 4,948,734 | 8/1990 | Edwards et al. | 435/252.5 |
| 5,045,314 | 9/1991 | Bone et al. . | |
| 5,093,120 | 5/1992 | Edwards et al. . | |
| 5,100,665 | 3/1992 | Hickle et al. . | |
| 5,151,363 | 9/1992 | Payne | 435/252.5 |
| 5,270,448 | 12/1993 | Payne | 530/350 |
| 5,350,577 | 9/1994 | Payne | 435/93.461 |

OTHER PUBLICATIONS

Prichard, R. K. et al. (1980) "The Problem of Anthelmintic Resistance in Nematodes" Australian Veterinary Journal 56:239–251.

Coles, G. C. (1986) "Anthelmintic Resistance in Sheep" Veterinary Clinics of North America: Food Animal Practice 2(2):423–432.

Bottjer, K. P., L. W. Bone, S. S. Gill (1985) "Nematoda: Susceptibility of the Egg to Bacillus thuringiensis Toxins" Experimental Parasitology 60:239–244.

Ignoffo, C. M., V. H. Dropkin (1977) "Deleterious Effects of the Thermostable Toxin of Bacillus thuringiensis on Species of Soil–Inhabiting, Myceliophagus, and Plant–Parasitic Nematodes" Journal of the Kansas Entomological Society 50(3):394–398.

Ciordia, H., W. E. Bizzell (1961) "A Preliminary Report on the Effects of Bacillus thuringiensis var. thuringiensis Berliner on the Development of the Free–Living Stages of Some Cattle Nematodes" Journal of Parisitology 47:41, abstract No. 86.

Meadows, J. et al. (1990) "Bacillus thuringiensis Strains Affect Population Growth of the Free–living Nematode Turbatrix–aceti" Intertebr. Reprod. Dev. 17(1):73–76 (Abstract only).

Medows, J. R. et al. (1989) "Lethality of Bacillus thuringiensis–morrisoni for Eggs of Trichostronglylus–Colubrigormis Nematoda" Invertebr. Reprod. Dev. 15(2):159–161 (Abstract only).

Meadows, J. et al. (1989) "Factors Influencing Lethality of Bacillus thuringiensis–kurstaki toxin for Eggs and Larvae of Trochostrongylus–Colubriformis Nematoda" J. Parasitol 75(2):191–194, (Abstract only).

Bone, L. W. et al. (1987) "Alteration of Trichostrongylus–colubroformis Egg Permeability by Bacillus thuringiensis–israelensis Toxin" J. Parasitol. 73(2):295–299, (Abstract only).

Primary Examiner—Debra S. Brittingham
Attorney, Agent, or Firm—Saliwanchik & Saliwanchik

[57] ABSTRACT

Novel B.t. genes encoding toxins active against nematode pests have been cloned. The DNA encoding the B.t. toxin can be used to transform various hosts to express the B.t. toxin.

8 Claims, 2 Drawing Sheets

5,589,382

SEQUENCE LISTING ( 1 ) GENERAL INFORMATION:

( i i i ) NUMBER OF SEQUENCES: 6

(2) INFORMATION FOR SEQ ID NO:1:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:1:

```
GGACCAGGAT TTACAGGWGG RRA                                              23
```

(2) INFORMATION FOR SEQ ID NO:2:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:2:

```
TAACGTGTAT WCGSTTTTAA TTTWGAYTC                                        29
```

(2) INFORMATION FOR SEQ ID NO:3:

(i) SEQUENCE CHARACTERISTICS:
        (A) LENGTH: 3561 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
ATGGATTGTA ATTTACAATC ACAACAAAAT ATTCCTTATA ATGTATTAGC AATACCAGTA        60
TCTAATGTTA ATGCGTTGGT TGATACAGCT GGAGATTTAA AAAAAGCATG GAAGAATTT        120
CAAAAAACTG GTTCTTTTTC ATTAACAGCT TTACAACAAG GATTTCTGC CTCACAAGGA        180
GGAGCATTCA ATTATTTAAC ATTATTACAA TCAGGAATAT CATTAGCTGG TTCTTTTGTC       240
CCTGGAGGTA CTTTTGTAGC ACCCATTGTT AATATGGTTA TTGGTTGGTT ATGGCCACAT       300
AAAAACAAGA CAGCGGATAC AGAAAATTTA ATAAAATTAA TTGATGAAGA AATTCAAAAA       360
CAATTAAACA AAGCCTTATT AGACCAAGAT AGAAACAATT GGACCTCTTT TTTAGAAAGT       420
ATATTTGATA CTTCAGCTAC AGTAAGTAAT GCAATTATAG ATGCACAGTG GTCAGGTACT       480
GTAGATACTA CAAATAGACA ACAAAAAACT CCAACAACAT CAGATTATCT AAATGTTGTT       540
GGAAAATTTG ATTCAGCGGA TTCTTCAATT ATAACTAATG AAAATCAAAT AATGAATGGC       600
AACTTTGACG TAGCTGCAGC ACCCTATTTT GTTATAGGAG CAACATTACG TCTTTCATTA       660
TATCAATCTT ATATTAAATT TTGTAATAGT TGGATTGATG CAGTTGGATT TAGTACAAAT       720
GATGCTAATA CACAAAAAGC TAATTTAGCT CGTACGAAAT TAACTATGCG TACTACAATT       780
AATGAATATA CACAAGAGT TATGAAAGTT TTTAAAGATT CCAAGAATAT GCCTACAATA        840
GGTACTAATA AATTTAGTGT TGATGCTTAT AATGTATATG TTAAAGGAAT GACATTAAAT       900
GTTTTAGATA TGGTAGCAAT ATGGTCTTCA TTATATCCAA ATGATTATAC TTCACAAACA       960
GCCATAGAAC AAACACGTGT CACTTTTTCA AATATGGTTG GACAAGAAGA AGGTACAGAT      1020
GGAACCCTAA AAATTTACAA TACTTTTGAT TCTCTTAGTT ATCAACATAG CCTAATACCT      1080
AATAATAATG TTAATTTAAT TTCTTATTAT ACTGATGAAT TGCAAAATCT AGAATTAGCA      1140
```

| | | | | | |
|---|---|---|---|---|---|
| GTATATACTC | CTAAAGGTGG | AAGTGGATAC | GCTTATCCTT | ATGGATTTAT | TTTAAATTAT | 1200 |
| GCAAACAGCA | ACTACAAATA | TGGTGATAAT | GATCCAACAG | GCAAACCATT | AAATAAACAA | 1260 |
| GATGGACCTA | TACAACAAAT | AAATGCAGCA | ACTCAAAACA | GTAAATATCT | AGATGGAGAA | 1320 |
| ACAATAAATG | GAATAGGGGC | ATCCTTACCT | GGTTATTGTA | CTACAGGATG | TTCAGCAACA | 1380 |
| GAACAACCTT | TTAGTTGTAC | TTCTACTGCT | AATAGCTATA | AGCAAGCTG | TAATCCTTCA | 1440 |
| GATACTAATC | AAAAATTAA | TGCTTTATAT | GCTTTACAC | AAACTAATGT | AAAGGGAAGC | 1500 |
| ACGGGGAAAT | TAGGAGTACT | GGCAAGTCTT | GTTCCATATG | ATTTAAATCC | TAAAAATGTA | 1560 |
| TTTGGTGAAT | TAGATTCAGA | TACAAATAAT | GTTATCTTAA | AAGGAATTCC | TGCAGAAAAA | 1620 |
| GGGTATTTTC | CTAATAATGC | GCGACCTACT | GTTGTAAAAG | AATGGATTAA | TGGTGCAAGT | 1680 |
| GCTGTACCAT | TTTATTCAGG | AAATACTTTA | TTTATGACGG | CTACGAATTT | AACAGCTACT | 1740 |
| CAATATAAAA | TTAGAATACG | TTATGCAAAT | CCAAATTCAG | ATACTCAAAT | CGGTGTACTA | 1800 |
| ATTACGCAAA | ATGGTTCTCA | AATTTCCAAT | AGTAATCTAA | CACTTTATAG | TACTACTGAT | 1860 |
| TCAAGTATGA | GTAGTAATTT | ACCACAAAAT | GTATATGTCA | CAGGGGAAAA | TGGAAATTAT | 1920 |
| ACACTTCTAG | ATTTATATAG | TACTACTAAT | GTTTTATCAA | CAGGAGATAT | TACATTAAAA | 1980 |
| CTTACAGGAG | GAAATCAAAA | AATATTTATT | GATCGAATAG | AATTTATTCC | TACTATGCCT | 2040 |
| GTACCTGCTC | CTACTAATAA | CACTAATAAC | AATAACGGCG | ATAACGGCAA | TAACAATCCC | 2100 |
| CCACACCACG | GTTGTGCAAT | AGCTGGTACA | CAACAACTTT | GTTCTGGACC | ACCTAAGTTT | 2160 |
| GAACAAGTAA | GTGATTTAGA | AAAAATTACA | ACGCAAGTAT | ATATGTTATT | CAAATCTTCT | 2220 |
| TCGTATGAAG | AATTAGCTCT | AAAAGTTTCT | AGCTATCAAA | TTAATCAAGT | GGCATTGAAA | 2280 |
| GTTATGGCAC | TATCTGATGA | AAAGTTTTGT | GAAGAAAAAA | GATTGTTACG | AAAATTAGTC | 2340 |
| AATAAAGCAA | ACCAATTACT | AGAAGCACGT | AACTTACTAG | TAGGTGGAAA | TTTTGAAACA | 2400 |
| ACTCAAAATT | GGGTACTTGG | AACAAATGCT | TATATAAATT | ATGATTCGTT | TTTATTTAAT | 2460 |
| GGAAATTATT | TATCCTTACA | ACCAGCAAGT | GGATTTTTCA | CATCTTATGC | TTATCAAAAA | 2520 |
| ATAGATGAGT | CAACATTAAA | ACCATATACA | CGATATAAAG | TTTCTGGATT | CATTGGGCAA | 2580 |
| AGTAATCAAG | TAGAACTTAT | TATTTCTCGT | TATGGAAAAG | AAATTGATAA | AATATTAAAT | 2640 |
| GTTCCATATG | CAGGGCCTCT | TCCTATTACT | GCTGATGCAT | CGATAACTTG | TTGTGCACCA | 2700 |
| GAAATAGACC | AATGTGATGG | GGGGCAATCT | GATTCTCATT | TCTTCAACTA | TAGCATCGAT | 2760 |
| GTAGGTGCAC | TTCACCCAGA | ATTAAACCCT | GGCATTGAAA | TTGGTCTTAA | AATTGTGCAA | 2820 |
| TCAAATGGTT | ATATAACAAT | TAGTAATCTA | GAAATTATTG | AAGAACGTCC | ACTTACAGAA | 2880 |
| ATGGAAATTC | AAGCAGTCAA | TCGAAAAGAT | CACAAATGGA | AAAGAGAAAA | ACTTCTAGAA | 2940 |
| TGTGCAAGTG | TTAGTGAACT | TTTACAACCA | ATCATTAATC | AAATCGATTC | ATTGTTCAAA | 3000 |
| GATGCAAACT | GGTATAATGA | TATTCTTCCT | CATGTCACAT | ATCAAACTCT | AAAAAATATT | 3060 |
| ATAGTACCCG | ATTTACCAAA | ATTAAAACAT | TGGTTCATAG | ATCATCTCCC | AGGTGAATAT | 3120 |
| CATGAAATTG | AACAACAAAT | GAAGAAGCT | CTAAAACATG | CATTTACACA | ATTAGACGAG | 3180 |
| AAAAATTTAA | TCCACAATGG | TCACTTTGCA | ACTAACTTAA | TAGATTGGCA | AGTAGAAGGT | 3240 |
| GATGCTCGAA | TGAAAGTATT | AGAAAATAAT | GCTTTGGCAT | TACAACTTTC | CAATTGGGAT | 3300 |
| TCTAGTGTTT | CACAATCTAT | TGATATATTA | GAATTTGATG | AAGATAAAGC | ATATAAACTT | 3360 |
| CGCGTATATG | CTCAAGGAAG | CGGAACAATC | CAATTTGGAA | ACTGTGAAGA | TGAAGCCATC | 3420 |
| CAATTTAATA | CAAACTCATT | CGTATATAAA | GAAAAAATAA | TCTATTTCGA | TACCCCATCA | 3480 |
| ATTAACTTAC | ACATACAATC | AGAAGGTTCT | GAATTCGTTG | TAAGTAGTAT | CGACCTCGTT | 3540 |

GAATTATCAG ACGACGAATA A   3561

( 2 ) INFORMATION FOR SEQ ID NO:4:

( i ) SEQUENCE CHARACTERISTICS:
        ( A ) LENGTH: 1186 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met  Asp  Cys  Asn  Leu  Gln  Ser  Gln  Gln  Asn  Ile  Pro  Tyr  Asn  Val  Leu
 1              5                        10                       15
Ala  Ile  Pro  Val  Ser  Asn  Val  Asn  Ala  Leu  Val  Asp  Thr  Ala  Gly  Asp
               20                  25                       30
Leu  Lys  Lys  Ala  Trp  Glu  Glu  Phe  Gln  Lys  Thr  Gly  Ser  Phe  Ser  Leu
          35                  40                       45
Thr  Ala  Leu  Gln  Gln  Gly  Phe  Ser  Ala  Ser  Gln  Gly  Gly  Ala  Phe  Asn
     50                       55                  60
Tyr  Leu  Thr  Leu  Leu  Gln  Ser  Gly  Ile  Ser  Leu  Ala  Gly  Ser  Phe  Val
65                       70                  75                            80
Pro  Gly  Gly  Thr  Phe  Val  Ala  Pro  Ile  Val  Asn  Met  Val  Ile  Gly  Trp
                    85                  90                            95
Leu  Trp  Pro  His  Lys  Asn  Lys  Thr  Ala  Asp  Thr  Glu  Asn  Leu  Ile  Lys
               100                      105                 110
Leu  Ile  Asp  Glu  Glu  Ile  Gln  Lys  Gln  Leu  Asn  Lys  Ala  Leu  Leu  Asp
          115                      120                 125
Gln  Asp  Arg  Asn  Asn  Trp  Thr  Ser  Phe  Leu  Glu  Ser  Ile  Phe  Asp  Thr
     130                      135                 140
Ser  Ala  Thr  Val  Ser  Asn  Ala  Ile  Ile  Asp  Ala  Gln  Trp  Ser  Gly  Thr
145                      150                 155                           160
Val  Asp  Thr  Thr  Asn  Arg  Gln  Gln  Lys  Thr  Pro  Thr  Thr  Ser  Asp  Tyr
                    165                      170                 175
Leu  Asn  Val  Val  Gly  Lys  Phe  Asp  Ser  Ala  Asp  Ser  Ser  Ile  Ile  Thr
               180                      185                 190
Asn  Glu  Asn  Gln  Ile  Met  Asn  Gly  Asn  Phe  Asp  Val  Ala  Ala  Ala  Pro
          195                      200                 205
Tyr  Phe  Val  Ile  Gly  Ala  Thr  Leu  Arg  Leu  Ser  Leu  Tyr  Gln  Ser  Tyr
     210                      215                 220
Ile  Lys  Phe  Cys  Asn  Ser  Trp  Ile  Asp  Ala  Val  Gly  Phe  Ser  Thr  Asn
225                      230                 235                           240
Asp  Ala  Asn  Thr  Gln  Lys  Ala  Asn  Leu  Ala  Arg  Thr  Lys  Leu  Thr  Met
                    245                      250                 255
Arg  Thr  Thr  Ile  Asn  Glu  Tyr  Thr  Gln  Arg  Val  Met  Lys  Val  Phe  Lys
               260                      265                 270
Asp  Ser  Lys  Asn  Met  Pro  Thr  Ile  Gly  Thr  Asn  Lys  Phe  Ser  Val  Asp
          275                      280                 285
Ala  Tyr  Asn  Val  Tyr  Val  Lys  Gly  Met  Thr  Leu  Asn  Val  Leu  Asp  Met
     290                      295                 300
Val  Ala  Ile  Trp  Ser  Ser  Leu  Tyr  Pro  Asn  Asp  Tyr  Thr  Ser  Gln  Thr
305                      310                 315                           320
Ala  Ile  Glu  Gln  Thr  Arg  Val  Thr  Phe  Ser  Asn  Met  Val  Gly  Gln  Glu
                    325                      330                 335
Glu  Gly  Thr  Asp  Gly  Thr  Leu  Lys  Ile  Tyr  Asn  Thr  Phe  Asp  Ser  Leu
               340                      345                 350
```

```
Ser  Tyr  Gln  His  Ser  Leu  Ile  Pro  Asn  Asn  Val  Asn  Leu  Ile  Ser
          355                 360                 365

Tyr  Tyr  Thr  Asp  Glu  Leu  Gln  Asn  Leu  Glu  Leu  Ala  Val  Tyr  Thr  Pro
     370                      375                 380

Lys  Gly  Gly  Ser  Gly  Tyr  Ala  Tyr  Pro  Tyr  Gly  Phe  Ile  Leu  Asn  Tyr
385                      390                 395                           400

Ala  Asn  Ser  Asn  Tyr  Lys  Tyr  Gly  Asp  Asn  Asp  Pro  Thr  Gly  Lys  Pro
               405                      410                      415

Leu  Asn  Lys  Gln  Asp  Gly  Pro  Ile  Gln  Gln  Ile  Asn  Ala  Ala  Thr  Gln
               420                 425                      430

Asn  Ser  Lys  Tyr  Leu  Asp  Gly  Glu  Thr  Ile  Asn  Gly  Ile  Gly  Ala  Ser
               435                 440                      445

Leu  Pro  Gly  Tyr  Cys  Thr  Thr  Gly  Cys  Ser  Ala  Thr  Glu  Gln  Pro  Phe
     450                 455                      460

Ser  Cys  Thr  Ser  Thr  Ala  Asn  Ser  Tyr  Lys  Ala  Ser  Cys  Asn  Pro  Ser
465                      470                 475                           480

Asp  Thr  Asn  Gln  Lys  Ile  Asn  Ala  Leu  Tyr  Ala  Phe  Thr  Gln  Thr  Asn
               485                      490                      495

Val  Lys  Gly  Ser  Thr  Gly  Lys  Leu  Gly  Val  Leu  Ala  Ser  Leu  Val  Pro
               500                      505                      510

Tyr  Asp  Leu  Asn  Pro  Lys  Asn  Val  Phe  Gly  Glu  Leu  Asp  Ser  Asp  Thr
          515                      520                      525

Asn  Asn  Val  Ile  Leu  Lys  Gly  Ile  Pro  Ala  Glu  Lys  Gly  Tyr  Phe  Pro
     530                      535                 540

Asn  Asn  Ala  Arg  Pro  Thr  Val  Val  Lys  Glu  Trp  Ile  Asn  Gly  Ala  Ser
545                      550                      555                      560

Ala  Val  Pro  Phe  Tyr  Ser  Gly  Asn  Thr  Leu  Phe  Met  Thr  Ala  Thr  Asn
                    565                      570                      575

Leu  Thr  Ala  Thr  Gln  Tyr  Lys  Ile  Arg  Ile  Arg  Tyr  Ala  Asn  Pro  Asn
               580                      585                      590

Ser  Asp  Thr  Gln  Ile  Gly  Val  Leu  Ile  Thr  Gln  Asn  Gly  Ser  Gln  Ile
          595                      600                      605

Ser  Asn  Ser  Asn  Leu  Thr  Leu  Tyr  Ser  Thr  Thr  Asp  Ser  Ser  Met  Ser
     610                      615                      620

Ser  Asn  Leu  Pro  Gln  Asn  Val  Tyr  Val  Thr  Gly  Glu  Asn  Gly  Asn  Tyr
625                      630                      635                      640

Thr  Leu  Leu  Asp  Leu  Tyr  Ser  Thr  Thr  Asn  Val  Leu  Ser  Thr  Gly  Asp
               645                      650                      655

Ile  Thr  Leu  Lys  Leu  Thr  Gly  Gly  Asn  Gln  Lys  Ile  Phe  Ile  Asp  Arg
               660                      665                      670

Ile  Glu  Phe  Ile  Pro  Thr  Met  Pro  Val  Pro  Ala  Pro  Thr  Asn  Asn  Thr
          675                      680                      685

Asn  Asn  Asn  Asn  Gly  Asp  Asn  Gly  Asn  Asn  Asn  Pro  Pro  His  His  Gly
     690                      695                      700

Cys  Ala  Ile  Ala  Gly  Thr  Gln  Gln  Leu  Cys  Ser  Gly  Pro  Pro  Lys  Phe
705                      710                 715                           720

Glu  Gln  Val  Ser  Asp  Leu  Glu  Lys  Ile  Thr  Thr  Gln  Val  Tyr  Met  Leu
               725                      730                      735

Phe  Lys  Ser  Ser  Ser  Tyr  Glu  Glu  Leu  Ala  Leu  Lys  Val  Ser  Ser  Tyr
          740                      745                      750

Gln  Ile  Asn  Gln  Val  Ala  Leu  Lys  Val  Met  Ala  Leu  Ser  Asp  Glu  Lys
          755                      760                      765

Phe  Cys  Glu  Glu  Lys  Arg  Leu  Leu  Arg  Lys  Leu  Val  Asn  Lys  Ala  Asn
```

|   |     |     |     |     | 770 |     |     |     |     | 775 |     |     |     |     | 780 |     |
|---|-----|-----|-----|-----|-----|-----|-----|-----|-----|-----|-----|-----|-----|-----|-----|-----|

Gln Leu Leu Glu Ala Arg Asn Leu Leu Val Gly Gly Asn Phe Glu Thr
785                 790                 795                 800

Thr Gln Asn Trp Val Leu Gly Thr Asn Ala Tyr Ile Asn Tyr Asp Ser
            805                 810                 815

Phe Leu Phe Asn Gly Asn Tyr Leu Ser Leu Gln Pro Ala Ser Gly Phe
            820                 825                 830

Phe Thr Ser Tyr Ala Tyr Gln Lys Ile Asp Glu Ser Thr Leu Lys Pro
            835                 840                 845

Tyr Thr Arg Tyr Lys Val Ser Gly Phe Ile Gly Gln Ser Asn Gln Val
    850                 855                 860

Glu Leu Ile Ile Ser Arg Tyr Gly Lys Glu Ile Asp Lys Ile Leu Asn
865                 870                 875                 880

Val Pro Tyr Ala Gly Pro Leu Pro Ile Thr Ala Asp Ala Ser Ile Thr
            885                 890                 895

Cys Cys Ala Pro Glu Ile Asp Gln Cys Asp Gly Gln Ser Asp Ser
            900                 905                 910

His Phe Phe Asn Tyr Ser Ile Asp Val Gly Ala Leu His Pro Glu Leu
            915                 920                 925

Asn Pro Gly Ile Glu Ile Gly Leu Lys Ile Val Gln Ser Asn Gly Tyr
    930                 935                 940

Ile Thr Ile Ser Asn Leu Glu Ile Ile Glu Glu Arg Pro Leu Thr Glu
945                 950                 955                 960

Met Glu Ile Gln Ala Val Asn Arg Lys Asp His Lys Trp Lys Arg Glu
            965                 970                 975

Lys Leu Leu Glu Cys Ala Ser Val Ser Glu Leu Leu Gln Pro Ile Ile
            980                 985                 990

Asn Gln Ile Asp Ser Leu Phe Lys Asp Ala Asn Trp Tyr Asn Asp Ile
        995                 1000                1005

Leu Pro His Val Thr Tyr Gln Thr Leu Lys Asn Ile Ile Val Pro Asp
    1010                1015                1020

Leu Pro Lys Leu Lys His Trp Phe Ile Asp His Leu Pro Gly Glu Tyr
1025                1030                1035                1040

His Glu Ile Glu Gln Gln Met Lys Glu Ala Leu Lys His Ala Phe Thr
            1045                1050                1055

Gln Leu Asp Glu Lys Asn Leu Ile His Asn Gly His Phe Ala Thr Asn
        1060                1065                1070

Leu Ile Asp Trp Gln Val Glu Gly Asp Ala Arg Met Lys Val Leu Glu
        1075                1080                1085

Asn Asn Ala Leu Ala Leu Gln Leu Ser Asn Trp Asp Ser Ser Val Ser
    1090                1095                1100

Gln Ser Ile Asp Ile Leu Glu Phe Asp Glu Asp Lys Ala Tyr Lys Leu
1105                1110                1115                1120

Arg Val Tyr Ala Gln Gly Ser Gly Thr Ile Gln Phe Gly Asn Cys Glu
            1125                1130                1135

Asp Glu Ala Ile Gln Phe Asn Thr Asn Ser Phe Val Tyr Lys Glu Lys
        1140                1145                1150

Ile Ile Tyr Phe Asp Thr Pro Ser Ile Asn Leu His Ile Gln Ser Glu
    1155                1160                1165

Gly Ser Glu Phe Val Val Ser Ser Ile Asp Leu Val Glu Leu Ser Asp
    1170                1175                1180

Asp Glu
1185

( 2 ) INFORMATION FOR SEQ ID NO:5:

( i ) SEQUENCE CHARACTERISTICS:
        ( A ) LENGTH: 3504 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
ATGACAAATC CAACTATACT ATATCCTAGT TACCATAATG TATTAGCTCA TCCGATTAGA          60
TTAGATTCTT TTTTTGATCC ATTTGTAGAG ACATTTAAGG ATTTAAAAGG GGCTTGGGAA         120
GAATTCGGAA AAACGGGATA TATGGACCCC TTAAAACAAC ACCTTCAAAT CGCATGGGAT         180
ACTAGTCAAA ATGGAACAGT GGATTATTTA GCATTAACAA AAGCATCTAT ATCTCTCATA         240
GGTTTAATTC CTGGTGCAGA CGCTGTAGTC CCTTTTATTA ATATGTTTGT AGACTTTATT         300
TTTCCGAAAT TATTTGGAAG AGGTTCTCAA CAAAATGCTC AAGCTCAATT TTTCGAACTA         360
ATCATAGAAA AAGTTAAAGA ACTTGTTGAT GAAGATTTTA GAAACTTTAC CCTTAATAAT         420
CTACTCAATT ACCTTGATGG TATGCAAACA GCCTTATCAC ATTTCCAAAA CGATGTACAA         480
ATTGCTATTT GTCAAGGAGA ACAACCAGGA CTTATGCTAG ATCAAACACC AACGGCTTGT         540
ACTCCTACTA CAGACCATTT AATTTCTGTA AGAGAATCTT TAAAGATGC TCGAACTACA          600
ATTGAAACAG CTTTACCACA TTTTAAAAAT CCTATGCTAT CCACAAATGA TAACACTCCA         660
GATTTTAATA GCGACACTGT CTTATTAACA TTACCAATGT ATACAACAGG AGCGACTTTA         720
AATCTTATAT TACATCAAGG GTATATTCAA TTCGCAGAAA GATGGAAATC TGTAAATTAT         780
GATGAAAGTT TTATAAATCA AACAAAGTT GATTTGCAAC GTCGTATTCA GGACTATTCT          840
ACTACTGTAT CTACCACTTT TGAAAAATTC AAACCTACTC TAAATCCATC AAATAAAGAA         900
TCTGTTAATA AGTATAATAG ATATGTTCGT TCCATGACTC TTCAATCTTT AGACATTGCT         960
GCAACATGGC CTACTTTAGA TAATGTTAAT TACCCTTCCA ATGTAGATAT TCAATTGGAT        1020
CAAACTCGCT TAGTATTTTC AGATGTTGCA GGACCTTGGG AAGGTAATGA TAATATAACT        1080
TCGAATATTA TAGATGTATT AACACCAATA AATACAGGGA TAGGATTTCA AGAAAGTTCA        1140
GATCTTAGAA AATTCACTTA TCCACGAATA GAATTACAAA GCATGCAATT CCATGGACAA        1200
TATGTAAACT CAAAAAGTGT AGAACATTGT TATAGCGATG GTCTTAAATT AAATTATAAA        1260
AATAAAACTA TAACTGCAGG TGTAAGTAAT ATTGATGAAA GTAATCAAAA TAATAAACAT        1320
AACTATGGTC CTGTAATAAA TAGTCCTATT ACTGATATCA ACGTAAATTC CCAAAATTCT        1380
CAATATTTAG ATTTAAATTC AGTCATGGTA AATGGTGGTC AAAAAGTAAC CGGGTGTTCA        1440
CCACTTAGTT CAAATGGTAA TTCTAATAAT GCTGCTTTAC CTAATCAAAA AATAAATGTT        1500
ATTTATTCAG TACAATCAAA TGATAAACCA GAAAAACATG CAGACACTTA TAGAAAATGG        1560
GGATATATGA GCAGTCATAT TCCTTATGAT CTTGTTCCAG AAAATGTAAT TGGAGATATA        1620
GATCCGGATA CTAAACAACC GTCATTGCTT CTTAAAGGGT TTCCGGCAGA AAAAGGATAT        1680
GGTGACTCAA TTGCATATGT ATCAGAACCT TTAAATGGTG CGAATGCAGT TAAACTTACT        1740
TCATATCAAG TTCTCCAAAT GGAAGTTACA AATCAAACAA CTCAAAAATA TCGTATTCGC        1800
ATACGTTATG CTACAGGTGG AGATACAGCT GCTTCTATAT GGTTTCATAT TATTGGTCCA        1860
TCTGGAAATG ATTTAACAAA CGAAGGCCAT AACTTCTCTA GTGTATCTTC TAGAAATAAA        1920
ATGTTTGTTC AGGGTAATAA CGGAAAATAT GTATTGAACA TCCTTACAGA TTCAATAGAA        1980
TTACCATCAG GACAACAAAC TATTCTTATT CAAATACTA ATTCTCAAGA TCTTTTTTTA         2040
```

| | | | | | |
|---|---|---|---|---|---|
| GATCGTATTG | AATTTATTTC | TCTCCCTTCT | ACTTCTACTC | CTACTTCTAC | TAATTTTGTA | 2100 |
| GAACCTGAAT | CATTAGAAAA | GATCATAAAC | CAAGTTAATC | AATTATTTAG | CTCCTCATCT | 2160 |
| CAAACTGAAT | TGGCTCACAC | TGTAAGCGAT | TATAAAATTG | ATCAAGTAGT | GCTAAAAGTA | 2220 |
| AATGCCTTAT | CCGACGATGT | ATTTGGTGTA | GAGAAAAAAG | CATTACGTAA | ACTTGTGAAT | 2280 |
| CAGGCCAAAC | AACTCAGTAA | AGCACGAAAT | GTATTGGTCG | GTGGAAACTT | TGAAAAAGGT | 2340 |
| CATGAATGGG | CACTAAGCCG | TGAAGCAACA | ATGGTCGCAA | ATCATGAGTT | ATTCAAAGGG | 2400 |
| GATCATTTAT | TATTACCACC | ACCAACCCTA | TATCCATCGT | ATGCATATCA | AAAAATTGAT | 2460 |
| GAATCGAAAT | TAAAATCCAA | TACACGTTAT | ACTGTTTCCG | GCTTTATTGC | GCAAAGTGAA | 2520 |
| CATCTAGAAG | TCGTTGTGTC | TCGATACGGG | AAAGAAGTAC | ATGACATGTT | AGATATCCCG | 2580 |
| TATGAAGAAG | CCTTACCAAT | TTCTTCTGAT | GAGAGTCCAA | ATTGTTGCAA | ACCAGCTGCT | 2640 |
| TGTCAGTGTT | CATCTTGTGA | TGGTAGTCAA | TCAGATTCTC | ATTTCTTTAG | CTATAGTATC | 2700 |
| GATGTTGGTT | CCCTACAATC | AGATGTAAAT | CTCGGCATTG | AATTCGGTCT | TCGTATTGCG | 2760 |
| AAACCAAACG | GATTTGCGAA | AATCAGTAAT | CTAGAAATTA | AGAAGATCG | TCCATTAACA | 2820 |
| GAAAAGAAA | TCAAAAAGT | ACAACGTAAA | GAACAAAAT | GGAAAAAGC | ATTTAACCAA | 2880 |
| GAACAAGCCG | AAGTAGCGAC | AACACTCCAA | CCAACGTTAG | ATCAAATCAA | TGCTTTGTAT | 2940 |
| CAAAATGAAG | ATTGGAACGG | TTCCGTTCAC | CCGGCCAGTG | ACTATCAACA | TCTGTCCGCT | 3000 |
| GTTGTTGTAC | CAACGTTACC | AAAACAAAGA | CATTGGTTTA | TGGAGGGTCG | AGAAGGCGAA | 3060 |
| CATGTTGTTC | TGACGCAACA | ATTCCAACAA | GCATTGGATC | GTGCGTTCCA | ACAAATCGAA | 3120 |
| GAACAAAACT | TAATCCACAA | TGGTAATTTG | GCGAATGGAT | TAACAGATTG | GACTGTCACA | 3180 |
| GGAGATGCAC | AACTTACGAT | CTTTGACGAA | GATCCAGTAT | TAGAACTAGC | GCATTGGGAT | 3240 |
| GCAAGTATCT | CTCAAACCAT | TGAAATTATG | GATTTTGAAG | GAAGACACAG | AATACAAACT | 3300 |
| GCGTGTACGT | GGAAAAGGCA | AAGGAACAGT | TACCGTTCAA | CATGGAGGAA | GAGATTAGAA | 3360 |
| ACGATGACAT | TCAATACAAC | GAGTTTTACA | ACACAAGAAC | AAACCTTCTA | CTTCGAAGGA | 3420 |
| GATACAGTGG | ACGTACATGT | TCAATCAGAG | AATAACACAT | TCCTGATAGA | TAGTGTGGAA | 3480 |
| CTCATTGAAA | TCATAGAAGA | GTAA | | | | 3504 |

( 2 ) INFORMATION FOR SEQ ID NO:6:

( i ) SEQUENCE CHARACTERISTICS:
        ( A ) LENGTH: 1167 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met<br>1 | Thr | Asn | Pro | Thr<br>5 | Ile | Leu | Tyr | Pro | Ser<br>10 | Tyr | His | Asn | Val | Leu<br>15 | Ala |
| His | Pro | Ile | Arg<br>20 | Leu | Asp | Ser | Phe | Phe<br>25 | Asp | Pro | Phe | Val | Glu<br>30 | Thr | Phe |
| Lys | Asp | Leu<br>35 | Lys | Gly | Ala | Trp | Glu<br>40 | Glu | Phe | Gly | Lys | Thr<br>45 | Gly | Tyr | Met |
| Asp | Pro<br>50 | Leu | Lys | Gln | His | Leu<br>55 | Gln | Ile | Ala | Trp | Asp<br>60 | Thr | Ser | Gln | Asn |
| Gly<br>65 | Thr | Val | Asp | Tyr | Leu<br>70 | Ala | Leu | Thr | Lys | Ala<br>75 | Ser | Ile | Ser | Leu | Ile<br>80 |
| Gly | Leu | Ile | Pro | Gly | Ala | Asp | Ala | Val | Val | Pro | Phe | Ile | Asn | Met | Phe |

```
                                    85                              90                              95
Val  Asp  Phe  Ile  Phe  Pro  Lys  Leu  Phe  Gly  Arg  Gly  Ser  Gln  Gln  Asn
                    100                       105                     110

Ala  Gln  Ala  Gln  Phe  Phe  Glu  Leu  Ile  Ile  Glu  Lys  Val  Lys  Glu  Leu
          115                       120                     125

Val  Asp  Glu  Asp  Phe  Arg  Asn  Phe  Thr  Leu  Asn  Asn  Leu  Leu  Asn  Tyr
     130                       135                     140

Leu  Asp  Gly  Met  Gln  Thr  Ala  Leu  Ser  His  Phe  Gln  Asn  Asp  Val  Gln
145                      150                       155                          160

Ile  Ala  Ile  Cys  Gln  Gly  Glu  Gln  Pro  Gly  Leu  Met  Leu  Asp  Gln  Thr
                    165                       170                     175

Pro  Thr  Ala  Cys  Thr  Pro  Thr  Thr  Asp  His  Leu  Ile  Ser  Val  Arg  Glu
                    180                       185                     190

Ser  Phe  Lys  Asp  Ala  Arg  Thr  Thr  Ile  Glu  Thr  Ala  Leu  Pro  His  Phe
          195                       200                     205

Lys  Asn  Pro  Met  Leu  Ser  Thr  Asn  Asp  Asn  Thr  Pro  Asp  Phe  Asn  Ser
     210                       215                     220

Asp  Thr  Val  Leu  Leu  Thr  Leu  Pro  Met  Tyr  Thr  Thr  Gly  Ala  Thr  Leu
225                            230                       235                     240

Asn  Leu  Ile  Leu  His  Gln  Gly  Tyr  Ile  Gln  Phe  Ala  Glu  Arg  Trp  Lys
                    245                       250                     255

Ser  Val  Asn  Tyr  Asp  Glu  Ser  Phe  Ile  Asn  Gln  Thr  Lys  Val  Asp  Leu
                    260                       265                     270

Gln  Arg  Arg  Ile  Gln  Asp  Tyr  Ser  Thr  Thr  Val  Ser  Thr  Thr  Phe  Glu
          275                       280                     285

Lys  Phe  Lys  Pro  Thr  Leu  Asn  Pro  Ser  Asn  Lys  Glu  Ser  Val  Asn  Lys
     290                       295                     300

Tyr  Asn  Arg  Tyr  Val  Arg  Ser  Met  Thr  Leu  Gln  Ser  Leu  Asp  Ile  Ala
305                      310                       315                          320

Ala  Thr  Trp  Pro  Thr  Leu  Asp  Asn  Val  Asn  Tyr  Pro  Ser  Asn  Val  Asp
                    325                       330                     335

Ile  Gln  Leu  Asp  Gln  Thr  Arg  Leu  Val  Phe  Ser  Asp  Val  Ala  Gly  Pro
               340                       345                     350

Trp  Glu  Gly  Asn  Asp  Asn  Ile  Thr  Ser  Asn  Ile  Ile  Asp  Val  Leu  Thr
               355                       360                     365

Pro  Ile  Asn  Thr  Gly  Ile  Gly  Phe  Gln  Glu  Ser  Ser  Asp  Leu  Arg  Lys
     370                       375                     380

Phe  Thr  Tyr  Pro  Arg  Ile  Glu  Leu  Gln  Ser  Met  Gln  Phe  His  Gly  Gln
385                      390                       395                          400

Tyr  Val  Asn  Ser  Lys  Ser  Val  Glu  His  Cys  Tyr  Ser  Asp  Gly  Leu  Lys
               405                       410                     415

Leu  Asn  Tyr  Lys  Asn  Lys  Thr  Ile  Thr  Ala  Gly  Val  Ser  Asn  Ile  Asp
               420                       425                     430

Glu  Ser  Asn  Gln  Asn  Asn  Lys  His  Asn  Tyr  Gly  Pro  Val  Ile  Asn  Ser
          435                       440                     445

Pro  Ile  Thr  Asp  Ile  Asn  Val  Asn  Ser  Gln  Asn  Ser  Gln  Tyr  Leu  Asp
     450                       455                     460

Leu  Asn  Ser  Val  Met  Val  Asn  Gly  Gly  Gln  Lys  Val  Thr  Gly  Cys  Ser
465                      470                       475                          480

Pro  Leu  Ser  Ser  Asn  Gly  Asn  Ser  Asn  Ala  Ala  Leu  Pro  Asn  Gln
                    485                       490                     495

Lys  Ile  Asn  Val  Ile  Tyr  Ser  Val  Gln  Ser  Asn  Asp  Lys  Pro  Glu  Lys
               500                       505                     510
```

-continued

| | | | | | | | | | | | | | | |
|---|---|---|---|---|---|---|---|---|---|---|---|---|---|---|
| His | Ala | Asp<br>515 | Thr | Tyr | Arg | Lys<br>520 | Trp | Gly | Tyr | Met | Ser<br>525 | Ser | His | Ile | Pro |
| Tyr | Asp<br>530 | Leu | Val | Pro | Glu<br>535 | Asn | Val | Ile | Gly<br>540 | Asp | Ile | Asp | Pro | Asp | Thr |
| Lys<br>545 | Gln | Pro | Ser | Leu | Leu<br>550 | Leu | Lys | Gly | Phe | Pro<br>555 | Ala | Glu | Lys | Gly | Tyr<br>560 |
| Gly | Asp | Ser | Ile | Ala<br>565 | Tyr | Val | Ser | Glu | Pro<br>570 | Leu | Asn | Gly | Ala | Asn<br>575 | Ala |
| Val | Lys | Leu | Thr<br>580 | Ser | Tyr | Gln | Val | Leu<br>585 | Gln | Met | Glu | Val<br>590 | Thr | Asn | Gln |
| Thr | Thr | Gln<br>595 | Lys | Tyr | Arg | Ile | Arg<br>600 | Ile | Arg | Tyr | Ala | Thr<br>605 | Gly | Gly | Asp |
| Thr | Ala<br>610 | Ala | Ser | Ile | Trp | Phe<br>615 | His | Ile | Ile | Gly | Pro<br>620 | Ser | Gly | Asn | Asp |
| Leu<br>625 | Thr | Asn | Glu | Gly | His<br>630 | Asn | Phe | Ser | Ser | Val<br>635 | Ser | Ser | Arg | Asn | Lys<br>640 |
| Met | Phe | Val | Gln | Gly<br>645 | Asn | Asn | Gly | Lys | Tyr<br>650 | Val | Leu | Asn | Ile | Leu<br>655 | Thr |
| Asp | Ser | Ile | Glu<br>660 | Leu | Pro | Ser | Gly | Gln<br>665 | Gln | Thr | Ile | Leu | Ile<br>670 | Gln | Asn |
| Thr | Asn | Ser<br>675 | Gln | Asp | Leu | Phe | Leu<br>680 | Asp | Arg | Ile | Glu | Phe<br>685 | Ile | Ser | Leu |
| Pro | Ser<br>690 | Thr | Ser | Thr | Pro | Thr<br>695 | Ser | Thr | Asn | Phe | Val<br>700 | Glu | Pro | Glu | Ser |
| Leu<br>705 | Glu | Lys | Ile | Ile | Asn<br>710 | Gln | Val | Asn | Gln | Leu<br>715 | Phe | Ser | Ser | Ser | Ser<br>720 |
| Gln | Thr | Glu | Leu | Ala<br>725 | His | Thr | Val | Ser | Asp<br>730 | Tyr | Lys | Ile | Asp | Gln<br>735 | Val |
| Val | Leu | Lys | Val<br>740 | Asn | Ala | Leu | Ser | Asp<br>745 | Asp | Val | Phe | Gly | Val<br>750 | Glu | Lys |
| Lys | Ala | Leu<br>755 | Arg | Lys | Leu | Val | Asn<br>760 | Gln | Ala | Lys | Gln | Leu<br>765 | Ser | Lys | Ala |
| Arg | Asn<br>770 | Val | Leu | Val | Gly | Gly<br>775 | Asn | Phe | Glu | Lys | Gly<br>780 | His | Glu | Trp | Ala |
| Leu<br>785 | Ser | Arg | Glu | Ala | Thr<br>790 | Met | Val | Ala | Asn | His<br>795 | Glu | Leu | Phe | Lys | Gly<br>800 |
| Asp | His | Leu | Leu | Leu<br>805 | Pro | Pro | Pro | Thr | Leu<br>810 | Tyr | Pro | Ser | Tyr | Ala<br>815 | Tyr |
| Gln | Lys | Ile | Asp<br>820 | Glu | Ser | Lys | Leu | Lys<br>825 | Ser | Asn | Thr | Arg | Tyr<br>830 | Thr | Val |
| Ser | Gly | Phe<br>835 | Ile | Ala | Gln | Ser | Glu<br>840 | His | Leu | Glu | Val | Val<br>845 | Val | Ser | Arg |
| Tyr | Gly<br>850 | Lys | Glu | Val | His | Asp<br>855 | Met | Leu | Asp | Ile | Pro<br>860 | Tyr | Glu | Glu | Ala |
| Leu<br>865 | Pro | Ile | Ser | Ser | Asp<br>870 | Glu | Ser | Pro | Asn | Cys<br>875 | Cys | Lys | Pro | Ala | Ala<br>880 |
| Cys | Gln | Cys | Ser | Ser<br>885 | Cys | Asp | Gly | Ser | Gln<br>890 | Ser | Asp | Ser | His | Phe<br>895 | Phe |
| Ser | Tyr | Ser | Ile<br>900 | Asp | Val | Gly | Ser | Leu<br>905 | Gln | Ser | Asp | Val | Asn<br>910 | Leu | Gly |
| Ile | Glu | Phe<br>915 | Gly | Leu | Arg | Ile | Ala<br>920 | Lys | Pro | Asn | Gly | Phe<br>925 | Ala | Lys | Ile |
| Ser | Asn<br>930 | Leu | Glu | Ile | Lys | Glu<br>935 | Asp | Arg | Pro | Leu | Thr<br>940 | Glu | Lys | Glu | Ile |

| | | | | | | | | | | | | | | |
|---|---|---|---|---|---|---|---|---|---|---|---|---|---|---|
| Lys 945 | Lys | Val | Gln | Arg | Lys 950 | Glu | Gln | Lys | Trp 955 | Lys | Ala | Phe | Asn | Gln 960 |
| Glu | Gln | Ala | Glu | Val 965 | Ala | Thr | Thr | Leu | Gln 970 | Pro | Thr | Leu | Asp | Gln 975 | Ile |
| Asn | Ala | Leu | Tyr 980 | Gln | Asn | Glu | Asp | Trp 985 | Asn | Gly | Ser | Val | His 990 | Pro | Ala |
| Ser | Asp | Tyr 995 | Gln | His | Leu | Ser | Ala | Val 1000 | Val | Val | Pro | Thr 1005 | Leu | Pro | Lys |
| Gln | Arg 1010 | His | Trp | Phe | Met | Glu 1015 | Gly | Arg | Glu | Gly | His 1020 | Val | Val | Leu |
| Thr 1025 | Gln | Gln | Phe | Gln | Gln 1030 | Ala | Leu | Asp | Arg | Ala 1035 | Phe | Gln | Gln | Ile | Glu 1040 |
| Glu | Gln | Asn | Leu | Ile 1045 | His | Asn | Gly | Asn | Leu 1050 | Ala | Asn | Gly | Leu | Thr 1055 | Asp |
| Trp | Thr | Val | Thr 1060 | Gly | Asp | Ala | Gln | Leu 1065 | Thr | Ile | Phe | Asp | Glu 1070 | Asp | Pro |
| Val | Leu | Glu 1075 | Leu | Ala | His | Trp | Asp 1080 | Ala | Ser | Ile | Ser | Gln 1085 | Thr | Ile | Glu |
| Ile | Met 1090 | Asp | Phe | Glu | Gly | Arg 1095 | His | Arg | Ile | Gln | Thr 1100 | Ala | Cys | Thr | Trp |
| Lys 1105 | Arg | Gln | Arg | Asn | Ser 1110 | Tyr | Arg | Ser | Thr | Trp 1115 | Arg | Lys | Arg | Leu | Glu 1120 |
| Thr | Met | Thr | Phe | Asn 1125 | Thr | Thr | Ser | Phe | Thr 1130 | Thr | Gln | Glu | Gln | Thr 1135 | Phe |
| Tyr | Phe | Glu | Gly 1140 | Asp | Thr | Val | Asp | Val 1145 | His | Val | Gln | Ser | Glu 1150 | Asn | Asn |
| Thr | Phe | Leu 1155 | Ile | Asp | Ser | Val | Glu 1160 | Leu | Ile | Glu | Ile | Ile 1165 | Glu | Glu |

BACILLUS THURINGIENSIS GENES ENCODING NEMATODE-ACTIVE TOXINS

CROSS-REFERENCE TO RELATED APPLICATIONS

This application is a continuation-in-part of co-pending application Ser. No. 08/310,197, filed Sep. 21, 1994; which is a division of Ser. No. 08/092,155, filed Jul. 15, 1993, now U.S. Pat. No. 5,350,577; which is a division of Ser. No. 07/918,345, filed Jul. 21, 1992, now U.S. Pat. No. 5,270,448; which is a division of 07/558,738, filed Jul. 27, 1990, now U.S. Pat. No. 5,151,363. This application is also a continuation-in-part of co-pending application Ser. No. 08/357,698, filed Dec. 16, 1994; which is a division of Ser. No. 08/176,403, filed Dec. 30, 1993, now abandoned; which is a continuation-in-part of 07/999,053, filed Dec. 31, 1992, now abandoned.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering *B.t.* endotoxins to agricultural environments are under development, including the use of plants genetically engineered with endotoxin genes for insect resistance and the use of stabilized intact microbial cells as *B.t.* endotoxin delivery vehicles (Gaertner and Kim, 1988). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* var. *kurstaki* have been used for many years as commercial insecticides for lepidopteran pests. For example, *B. thuringiensis* var. *kurstaki* HD-1 produces a crystal called a δ-endotoxin which is toxic to the larvae of a number of lepidopteran insects.

In recent years, however, investigators have discovered *B.t.* pesticides with specificities for a much broader range of pests. For example, other species of *B.t.*, namely *B.t.* var. *israelensis* and *B.t.* var. *tenebrionis* (a.k.a. M-7, a.k.a. *B.t.* var. *san diego*), have been used commercially to control insects of the orders Diptera and Coleoptera, respectively (Gaertner, 1989). See also Couch, 1980 and Beegle, 1978. Krieg et al., 1983, describe *Bacillus thuringiensis* var. *tenebrionis*, which is reportedly active against two beetles in the order Coleoptera. These are the Colorado potato beetle, *Leptinotarsa decemlineata*, and the beetle *Agelastica alni*.

Recently, new subspecies of *B.t.* have been identified, and genes responsible for active δ-endotoxin proteins have been isolated (Höfte and Whiteley, 1989). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). Prefontaine et al., 1987, describe probes useful in classifying lepidopteran-active genes. The discovery of strains specifically toxic to other pests has been reported (Feitelson et al., 1992).

The cloning and expression of a *B.t.* crystal protein gene in *Escherichia coli* has been described in the published literature (Schnepf and Whiteley, 1981). U.S. Pat. No. 4,448,885 and U.S. Pat. No. 4,467,036 both disclose the expression of *B.t.* crystal proteins in *E. coli*. U.S. Pat. Nos. 4,797,276 and 4,853,331 disclose *B. thuringiensis* var. *tenebrionis* (a.k.a. *B.t. san diego*, a.k.a. M-7) which can be used to control coleopteran pests in various environments. U.S. Pat. No. 4,918,006 discloses *Bacillus thuringiensis* var. *israelensis* toxins which are active against dipteran pests. This patent reports that a protein of about 27 kD, and fragments thereof, are responsible for the dipteran activity. U.S. Pat. No. 4,849,217 discloses *B.t.* isolates which have activity against the alfalfa weevil. U.S. Pat. No. 5,151,363 and U.S. Pat. No. 4,948,734 disclose certain isolates of *B.t.* which have activity against nematodes.

The accepted methodology for control of nematodes has centered around the use of the drug benzimidazole and its congeners. The use of these drugs on a wide scale has led to many instances of resistance among nematode populations (Prichard et al., 1980; Coles, 1986). There are more than 100,000 described species of nematodes.

A small number of research articles have been published concerning the effects of δ-endotoxins from *B. thuringiensis* species on the viability of nematode eggs. Bottjer et al. (1985) have reported that *B.t. kurstaki* and *B.t. israelensis* were toxic *in vitro* to eggs of the nematode *Trichostrongylus colubriformis*. In addition, 28 other *B.t.* strains were tested with widely variable toxicities. The most potent had $LD_{50}$ values in the nanogram range. Ignoffo and Dropkin (1977) have reported that the thermostable toxin from *Bacillus thuringiensis* (beta exotoxin) was active against a free-living nematode, *Panagrellus redivivus* (Goodey); a plant-parasitic nematode, *Meloidogyne incognita* (Chitwood); and a fungus-feeding nematode, *Aphelenchus avena* (Bastien). Beta exotoxin is a generalized cytotoxic agent with little or no specificity. Also, Ciordia and Bizzell (1961) gave a preliminary report on the effects of *B. thuringiensis* on some cattle nematodes.

At the present time there is a need to have more effective means to control the many nematodes that cause considerable damage to susceptible hosts. Effective means would advantageously employ biological agents, such as *B.t.* pesticides. As a result of extensive research and investment of resources, many other patents have issued for new *B.t.* isolates and new uses of *B.t.* isolates. However, the discovery of new *B.t.* isolates and new uses of known *B.t.* isolates remains an empirical, unpredictable art.

BRIEF SUMMARY OF THE INVENTION

The subject invention concerns novel δ-endotoxin genes obtainable from *B.t.* isolates PS80JJ1, PS158D5, PS169E, PS177F1, PS177G, PS204G4, and PS204G6, wherein the genes encode proteins which are active against nematode pests. These toxin genes can be transferred to suitable hosts as described herein.

Further aspects of the subject invention concern nematode-active toxins, and fragments thereof, encoded by the genes disclosed herein. Another embodiment of the subject invention concerns hosts transformed with the genes of the subject invention. In a preferred embodiment, the transformed hosts are plants.

Figure 1A:
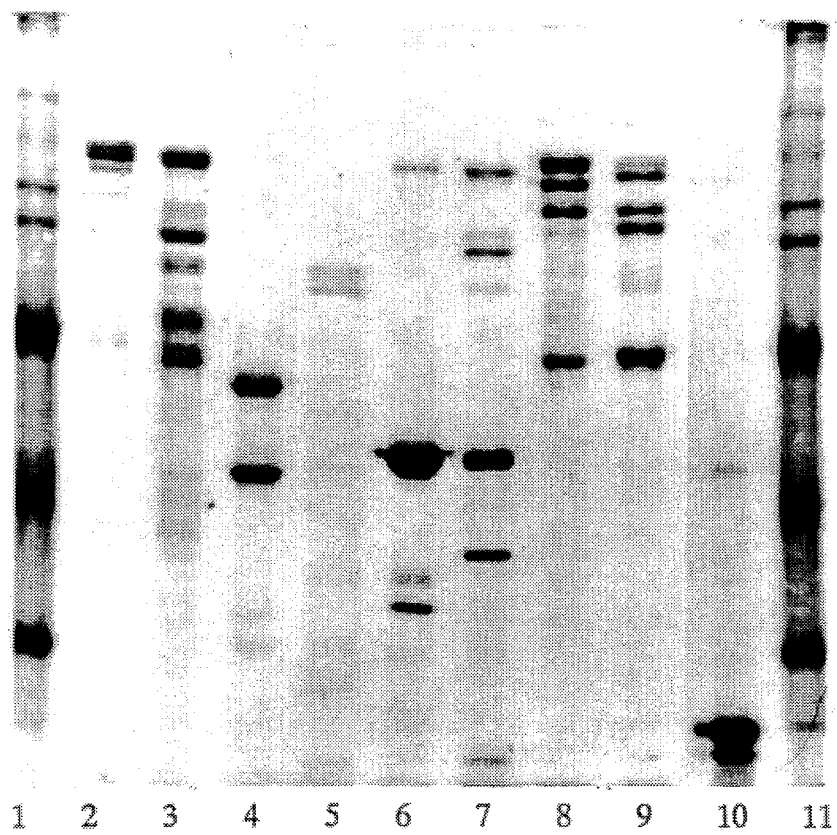
FIG. 1 is a photograph of 9% SDS polyacrylamide gel electrophoresis showing alkali-soluble proteins of nematode active strains.
Figure 1B:
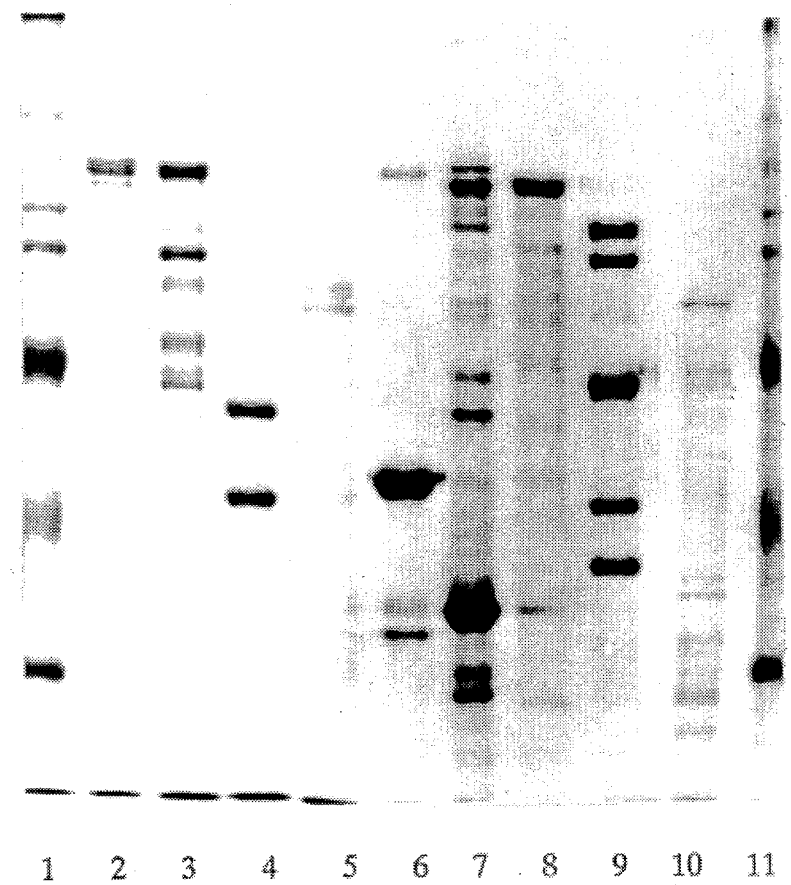

Gel A: Lane (1) Protein standard, (2) PS17, (3) PS33F2, (4) PS52A1, (5) PS63B, (6), PS69D1, (7) PS80JJ1, (8) PS177F1, (9) PS177G, (10) PS 204G6, (11) Protein standard.

Gel B: Lane (1) Protein standard, (2) PS17, (3) PS33F2, (4) PS52A1, (5) PS63B, (6), PS69D1, (7) PS169E, (8) PS167P, (9) PS204G4, (10) PS158 D5, (11) Protein standard.

BRIEF DESCRIPTION OF THE SEQUENCES

SEQ ID NO. 1 is the nucleotide sequence of a "forward" oligonucleotide primer used for PCR amplification of the 80JJ1 and 167P genes.

SEQ ID NO. 2 is the nucleotide sequence of a "reverse" oligonucleotide primer used for PCR amplification of the 80JJ1 and 167P genes.

SEQ ID NO. 3 is the nucleotide sequence of the 80JJ1 toxin gene.

SEQ ID NO. 4 is the amino acid sequence of the 80JJ1 protein.

SEQ ID NO. 5 is the nucleotide sequence of the 167P toxin gene.

SEQ ID NO. 6 is the amino acid sequence of the 167P protein.

DETAILED DISCLOSURE OF THE INVENTION

The subject invention pertains to novel genes which encode nematode-active toxins. The toxins themselves are also an important aspect of the invention. A further embodiment of the subject invention is the transformation of suitable hosts to confer upon these hosts the ability to express nematode-active toxins.

The *Bacillus thuringiensis* isolates from which the genes of the subject invention can be obtained have been deposited in the permanent collection of the Agricultural Research Service Patent Culture Collection (NRRL), Northern Regional Research Center, 1915 North University Street, Peoria, Ill. 61604, USA. The accession numbers are as follows:

| Culture | Repository No. | Deposit Date |
| --- | --- | --- |
| B.t. strain PS80JJ1 | NRRL B-18679 | July 17, 1990 |
| B.t. strain PS158D5 | NRRL B-18680 | July 17, 1990 |
| B.t. strain PS167P | NRRL B-18681 | July 17, 1990 |
| B.t. strain PS169E | NRRL B-18682 | July 17, 1990 |
| B.t. strain PS177F1 | NRRL B-18683 | July 17, 1990 |
| B.t. strain PS177G | NRRL B-18684 | July 17, 1990 |
| B.t. strain PS204G4 | NRRL B-18685 | July 17, 1990 |
| B.t. strain PS204G6 | NRRL B-18686 | July 17, 1990 |
| E. coli NM522 (pMYC2379) | NRRL B-21155 | November 3, 1993 |
| E. coli NM522 (pMYC2382) | NRRL B-21329 | September 28, 1994 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace the deposit(s) should the depository be unable to furnish a sample when requested, due to the condition of the deposit(s). All restrictions on the availability to the public of the subject culture deposits will be irrevocably removed upon the granting of a patent disclosing them.

Genes and toxins. The genes and toxins useful according to the subject invention include not only the full length sequences disclosed but also fragments of these sequences, variants, mutants, and fusion proteins which retain the characteristic pesticidal activity of the toxins specifically exemplified. In some instances, the fusion protein may contain, in addition to the characteristic pesticidal activity of the toxins specifically exemplified, another pesticidal activity contributed by the fusion process. As used herein, the terms "variants" or "variations" of genes refer to nucleotide sequences which encode the same toxins or which encode equivalent toxins having similar pesticidal activity. As used herein, the term "equivalent toxins" refers to toxins having the same or essentially the same biological activity against the target pests as the claimed toxins.

It should be apparent to a person skilled in this art that genes encoding nematode-active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from *B.t.* isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other *B.t.* toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" amino acid sequence refers to sequences which have amino acid substitutions, deletions, additions, or insertions which do not materially affect the pesticidal activity of the protein.

A further method for identifying the toxins and genes of the subject invention is through the use of oligonucleotide probes. These probes are nucleotide sequences having a means for detection. As is well known in the art, if the probe molecule and nucleic acid sample hybridize by forming a strong bond between the two molecules, it can be reasonably assumed that the probe and sample have substantial homology. The probe's means of detection provides a means for determining in a known manner whether hybridization has occurred. Such a probe analysis provides a rapid method for identifying toxin-encoding genes of the subject invention. The nucleotide segments which are used as probes according to the invention can be synthesized by use of DNA synthesizers using standard procedures. These nucleotide sequences can also be used as PCR primers to amplify genes of the subject invention.

Certain toxins of the subject invention have been specifically exemplified herein. Since these toxins are merely exemplary of the toxins of the subject invention, it should be readily apparent that the subject invention further comprises variant or equivalent toxins (and nucleotide sequences coding for equivalent toxins) having the same or essentially the same pesticidal activity of the exemplified toxins. These equivalent toxins can have amino acid homology with an exemplified toxin. This amino acid homology will typically be greater than 75%, preferably be greater than 90%, and most preferably be greater than 95%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions.

Recombinant hosts. The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested by the pest. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the *B.t.* toxin gene is introduced via a suitable vector into a microbial host, and said host is applied to the environment in a living state, it is advantageous to use certain host microbes. For example, microorganism hosts can be selected which are known to occupy the pest's habitat. Microorganism hosts may also live symbiotically with a specific species of pest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the habitat of pests. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, e.g., genera Metarhizium, Bavaria, Saccharomyces, Cryptococcus, Kluyveromyces, Sporobolomyces, Rhodotorula, and Aureobasidium. Of particular interest are such bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. As mentioned above, *B.t.* or recombinant cells expressing a *B.t.* toxin can be treated to prolong the toxin activity and stabilize the cell. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids, and Helly's fixative (See: Humason, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of cell treatment retains at least a substantial portion of the bio-availability or bioactivity of the toxin.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art and are used with commercial strains of B. thuringiensis (HD-1) active against Lepidoptera, e.g., caterpillars. The B.t. isolates (spores and crystals) of the subject invention can be used to control nematode pests.

The B.t. toxins of the invention can be administered orally in a unit dosage form such as a capsule, bolus or tablet, or as a liquid drench when used as an anthelmintic in mammals. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight, the capsules and boluses comprise the active ingredient admixed with a carrier vehicle such as starch, talc, magnesium stearate, or dicalcium phosphate.

Where it is desired to administer the toxin compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the nematode-active agent, depending upon the factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or, optionally, fed separately. Alternatively, the compounds may be administered to animals parenterally, for example, by intraluminal, intramuscular, intratracheal, or subcutaneous injection, in which event the active ingredient is dissolved or dispersed in a liquid carrier vehicle. For parenteral administration, the active material is suitably admixed with an acceptable vehicle, preferably of the vegetable oil variety, such as peanut oil, cotton seed oil and the like. Other parenteral vehicles, such as organic preparations using solketal, glycerol, formal and aqueous parenteral formulations, are also used. The active compound or compounds are dissolved or suspended in the parenteral formulation for administration; such formulations generally contain from 0.005 to 5% by weight of the active compound.

When the toxins are administered as a component of the feed of the animals, or dissolved or suspended in the drinking water, compositions are provided in which the active compound or compounds are intimately dispersed in an inert carrier or diluent. By inert carrier is meant one that will not react with the nematode-active agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like.

In addition to having anthelminthic activity within the digestive tract of mammals, spores from nematicidal B.t. isolates will pass through the animals' digestive tract, germinate and multiply in the feces, and thereby provide additional control of nematode larva which hatch and multiply therein.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the nematode pests, e.g., plants, soil, or water by spraying, dusting, sprinkling, or the like.

Mutants. Mutants of the B.t. isolates of the subject invention can be made by procedures well known in the art. For example, an asporogenous mutant can be obtained through ethylmethane sulfonate (EMS) mutagenesis. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Strains

A subculture of a B.t. strain can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Activity of *Bacillus thuringiensis* Isolates Against *Panagrellus redivivus*

Worms were collected in a tube and allowed to settle for about 15 minutes. The water was decanted and replaced with fresh water three or four times until the water remained clear. 250 μl rinsed nematodes (20–30 worms), and 100 μl of a spore/crystal suspension were added to 650 μl water in each well of a multi-well tray. Nematodes were counted and the numbers recorded. After four days, the live worms were counted and percent mortality calculated.

TABLE 2

| Bioassay results | |
|---|---|
| U.S. Pat. No. 4,948,734 | Mortality |
| B.t. strain No. | |
| PS17 | 90% |
| PS33F2 | 30% |
| PS52A1 | 100% |
| PS63B | 92% |
| PS69D1 | 100% |
| Novel B.t. strain No. | |
| PS80JJ1 | 99% |

TABLE 2-continued

Bioassay results

| U.S. Pat. No. 4,948,734 | Mortality |
|---|---|
| PS158D5 | 99% |
| PS167P | 96% |
| PS169E | 100% |
| PS177F1 | 96% |
| PS177G | 100% |
| PS204G4 | 100% |
| PS204G6 | 100% |
| Control | 0% |

Tables 3 and 4 show the molecular mass of the alkali-soluble proteins in each novel nematode-active strain, as compared to previously known B.t. strains.

TABLE 3

Previously known nematode-active strains

| B.t. Strain | Approximate Molecular Mass of Proteins (kDa) |
|---|---|
| PS17 | 155, 145, 135 |
| PS33F2 | 140, 94, 86, 68, 65, 62 |
| PS52A1 | 57, 45 |
| PS63B | 84, 82, 78 |
| PS69D1 | 135, 46, 32 |

TABLE 4

New Nematode-Active Strains

| Novel B.t. Strain | Approximate Molecular Mass of Proteins (kDa) |
|---|---|
| PS80JJ1 | 130, 90, 47, 37 |
| PS158D5 | 80 |
| PS167P | 120 |
| PS169E | 150, 128, 33 |
| PS177F1 | 140, 116, 103, 62 |
| PS177G | 135, 125, 107, 98, 62 |
| PS204G4 | 105, 98, 90, 60, 44, 37 |
| PS204G6 | 23, 21 |

EXAMPLE 3

Cloning and Expression of a of Novel Toxin Gene from *Bacillus thuringiensis* Strain PS80JJ1

Total cellular DNA was prepared from *Bacillus thuringiensis* (*B.t.*) cells grown to an optical density, at 600 nm, of 1.0. Cells were pelleted by centrifugation and resuspended in protoplast buffer (20 mg/ml lysozyme in 0.3 M sucrose, 25 mM Tris-Cl (pH 8.0), 25 mM EDTA). After incubation at 37° C. for 1 hour, protoplasts were lysed by two cycles of freezing and thawing. Nine volumes of a solution of 0.1 M NaCl, 0.1% SDS, 0.1 M Tris-Cl were added to complete lysis. The cleared lystate was extracted twice with phenol:chloroform (1:1). Nucleic acids were precipitated with two volumes of ethanol and pelleted by centrifugation. The pellet was resuspended in TE buffer and RNase was added to a final concentration of 50 µg/ml. After incubation at 37° C. for 1 hour, the solution was extracted once each with phenol:chloroform (1:1) and TE-saturated chloroform. DNA was precipitated from the aqueous phase by the addition of one-tenth volume of 3 M NaOAc and two volumes of ethanol. DNA was pelleted by centrifugation, washed with 70% ethanol, dried, and resuspended in TE buffer.

An approximately 700–800 bp DNA fragment from a novel PS80JJ1 130 kDa toxin gene was obtained by polymerase chain reaction (PCR) amplification using PS80JJ1 cellular DNA and the following primers:

| "Forward": | 5' GGACCAGGATTTACAGG(TA)GG(AG)(AG)A 3' (SEQ ID NO. 1) |
|---|---|
| "Reverse": | 5' TAACGTGTAT(AT)CG(CG)TTTTAATTT(TA)GA(CT)TC 3' (SEQ ID NO. 2). |

The DNA fragment was cloned into pBluescript S/K (Stratagene, LaJolla, Calif.) and partially sequenced by dideoxynucleotide DNA sequencing methodology (Sanger et al., 1977) using Sequenase (US Biochemicals, Cleveland, Ohio). DNA sequences unique to at least one PS80JJ1 toxin gene were identified by computer comparison with other known δ-endotoxin genes.

The 700–800 bp DNA fragment was radiolabelled with $^{32}$P and used in standard hybridizations of Southern blots of PS80JJ1 total cellular DNA. Hybridizing bands included an approximately 1.8 kbp EcoRI fragment and an approximately 9.5 kbp HindIII fragment. These hybridizing DNA bands contain toxin genes or restriction fragments of toxin genes from PS80JJ1.

A gene library was constructed from PS80JJ1 DNA partially digested with NdeII. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The NdeII inserts were ligated into BamHI-digested LambdaGem-11 (Promega, Madison, Wis.). Recombinant phage were packaged and plated on *E. coli* KW251 cells. Plaques were screened by hybridization with the probe described above. Hybridizing phage were plaque-purified and used to infect liquid cultures of *E. coli* KW251 cells for isolation of DNA by standard procedures (Maniatis et al.).

For subcloning the gene encoding the PS80JJ1 130 kDa toxin, preparative amounts of phage DNA were digested with XhoI and electrophoresed on an agarose gel. The approximately 12 kbp band containing the toxin gene was excised from the gel, electroeluted from the gel slice, and purified by ion exchange chromatography as described above. The purified DNA insert was ligated into XhoI-digested pHTBlueII (an *E. coli/B. thuringiensis* shuttle vector comprised of pBluescript S/K [Stratagene, La Jolla, Calif.] and the replication origin from a resident *B.t.* plasmid [Lereclus et al.]). The ligation mix was used to transform frozen, competent *E. coli* NM522 cells (ATCC 47000). β-galactosidase- transformants were screened by restriction digestion of alkaline lysate plasmid minipreps as above. The desired plasmid construct, pMYC2379, contains a toxin gene that is novel compared to other toxin genes containing insecticidal proteins.

The PS80JJ1 toxin gene encoded by pMYC2379 was sequenced using the ABI373 automated sequencing system and associated software. Sequence analysis of the toxin gene revealed that it encodes a protein of approximately 130,000 daltons, deduced from the DNA sequence. The nucleotide and deduced amino acid sequences are shown in SEQ ID NOS. 3 and 4, respectively.

pMYC2379 was introduced into the acrystalliferous (Cry⁻) *B.t.* host, CryB (A. Aronson, Purdue University, West Lafayette, Ind.), by electroporation. Expression of the 130 kDa toxin was demonstrated by SDS-PAGE analysis.

A subculture of *E. coli* NM522 containing plasmid pMYC2379 was deposited in the permanent collection of the Patent Culture Collection (NRRL), Regional Research Center, 1815 North University Street, Peoria, Ill. 61604 USA or Nov. 3, 1991. The accession number is NRRL B-21155.

EXAMPLE 4

Cloning and Expression of a Novel Toxin Gene from *Bacillus thuringiensis* PS167P Total cellular DNA was prepared as in Example 3.

An approximately 700–800 bp DNA fragment from novel PS167P 130 kDa toxin genes was obtained by polymerase chain reaction (PCR) amplification using PS167P cellular DNA and SEQ ID NOS. 1 and 2. This DNA fragment was cloned into pBluescript S/K (Stratagene, La Jolla, Calif.) and partially sequenced by dideoxynucleotide DNA sequencing methodology (Sanger et al., 1977) using Sequenase (U.S. Biochemicals, Cleveland, Ohio). DNA sequences unique to at least two PS167P toxin genes were identified by computer comparison with other known δ-endotoxin genes.

The 700–800 bp DNA fragment was radiolabelled with $^{32}$P and used in standard hybridizations of Southern blots of PS167P total cellular DNA. Hybridizing bands included approximately 1.8 kbp and 2.3 kbp EcoRI fragments and approximately 5.5 kbp and 8.0 kbp HindIII fragments. These DNA fragments contain toxin genes or restriction fragments of toxin genes unique to PS167P.

A gene library was constructed from PS167P DNA partially digested with NdeII. Partial restriction digests were fractionated by agarose gel electrophoresis. DNA fragments 9.3 to 23 kbp in size were excised from gel, electroeluted from the gel slice, purified on an Elutip-D ion exchange column (Schleicher and Schuell, Keene, N.H.), and recovered by ethanol precipitation. The NdeII inserts were ligated into BamHI-digested LambdaGem-11 (Promega, Madison, Wis.). Recombinant phage were packaged and plated on *E. coli* KW251 cells. Plaques were screened by hybridization with the probe described above. Hybridizing phage were plaque-purified and used to infect liquid cultures of *E. coli* KW251 cells for isolation of DNA by standard procedures (Maniatis et al., 1989).

Southern blot analysis revealed that one of the recombinant phage isolates contained an approximately 5 kbp SalI band that hybridized to the PS167P toxin gene probe. One of the SalI sites flanking the PS167P toxin gene resides in the phage vector DNA sequence, while the other flanking SalI site is located within the PS167P DNA insert. This SalI fragment was subcloned by standard methods into pBluescript S/K (Stratagene, San Diego, Calif.) for DNA sequence analysis. The DNA insert was subcloned further as a SacI-KpnI fragment into pHTBlueII (an *E. coli/B. thuringiensis* shuttle vector comprised of pBluescript S/K and the replication origin from a resident *B.t.* plasmid [Lereclus et al., 1989] to yield pMYC2382. To test expression of the PS167P toxin gene in *B.t.*, pMYC2382 was introduced into the acrystalliferous (Cry–) *B.t.* host, CryB (A. Aronson, Purdue University, West Lafayette, Ind.) by electroporation. Expression of the approximately 130 kDa PS167P toxin encoded by pMYC2382 was demonstrated by SDS-PAGE analysis.

The PS167P toxin gene encoded by pMYC2382 was sequenced using the ABI373 automated sequenceing system and associated software. The PS167P toxin nucleotide (SEQ ID NO. 5) and deduced amino acid (SEQ ID NO. 6) sequences are novel compared to other toxin genes encoding pesticidal proteins.

A subculture of *E. coli* NM522 containing plasmid pMYC2382 was deposited in the permanent collection of the Patent Culture Collection (NRRL), Regional Research Center, 1815 North University Street, Peoria, Ill. 61604 USA on Sep. 28, 1994. The accession number is NRRL B-21329.

EXAMPLE 5

Insertion of Toxin Genes Into Plants

One aspect of the subject invention is the transformation of plants with genes coding for a toxin active against nematode pests. The transformed plants are resistant to attack by nematodes.

Genes encoding nematode-active toxins, as disclosed herein, can be inserted into plant cells using a variety of techniques which are well known in the art. Those techniques include transformation with T-DNA using *Agrobacterium tumefaciens* or *Agrobacterium rhizogenes* as transformation agent, fusion, microinjection, bombardment, chemical agent (PEG) assisted DNA uptake, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al., 1978). The agrobacterium used as host cell is to comprise a plasmid carrying a vir region. The vir region is necessary for the transfer of the T-DNA into the plant cell.

The use of T-DNA for the transformation of plant cells has been intensively researched and sufficiently described in EP 120 516; Hoekema (1985); Fraley et at (1985); An et al. (1985).

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

The bacterium so transformed is used for the transformation of plant cells. Plant explants can advantageously be cultivated with *Agrobacterium tumefaciens* or *Agrobacte-*

*rium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of microinjection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 6

Cloning of Novel *B.t.* Genes Into Insect Viruses

A number of viruses are known to infect insects. These viruses include, for example, baculoviruses and entomopoxviruses. In one embodiment of the subject invention, nematode-active genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (1990) and Martens et al. (1990).

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Patents

U.S. Pat. No. 4,448,885.
U.S. Pat. No. 4,467,036.
U.S. Pat. No. 4,695,455.
U.S. Pat. No. 4,695,462.
U.S. Pat. No. 4,797,276.
U.S. Pat. No. 4,849,217.
U.S. Pat. No. 4,853,331.
U.S. Pat. No. 4,918,006.
U.S. Pat. No. 4,948,734.
U.S. Pat. No. 5,135,867.
U.S. Pat. No. 5,151,363.

Foreign Patent Documents

EP 120 516

Other References

An et al. (1985) *EMBO J.* 4:277–287.

Beegle, C. C., (1978) "Use of Entomogenous Bacteria in Agroecosystems," *Developments in Industrial Microbiology* 20:97–104.

Bottjer, Bone, and Gill (1985) *Experimental Parasitology* 60:239–244.

Ciordia, H., W. E. Bizzell (1961) *Jour. of Parasitology* 47:41 [abstract].

Coles, G. C. (1986) "Anthelmintic resistance in sheep," In *Veterinary Clinics of North America: Food Animal Practice*, Vol 2:423–432 (Herd, R. P., eds.) W. B. Saunders, New York.

Couch, T. L. (1980) "Mosquito Pathogenicity of *Bacillus thuringiensis* var. *israelensis*," *Developments in Industrial Microbiology* 22:61–76.

Feitelson, J. S., J. Payne, L. Kim (1992) *Bio/Technology* 10:271–275.

Fraley et al. (1985) *Crit. Rev. Plant Sci.* 4:1–46.

Gaertner, F. H. (1989) "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255.

Gaertner, F. H., L. Kim (1988) *TIBTECH* 6:S4–S7.

Hoekema (1985) In: *The Binary Plant Vector System*, Offsetdurkkerij Kanters B.V., Alblasserdam, Chapter 5.

Höfte, H., H. R. Whiteley (1989) *Microbiological Reviews* 52(2):242–255.

Holsters et al. (1978) *Mol. Gen. Genet.* 163:181–187.

Humason, Gretchen L., *Animal Tissue Techniques*, W. H. Freeman and Company, 1967.

Ignoffo, C. M. and Dropkin, V. H. (1977) *J. Kans. Entomol. Soc.* 50:394–398.

Krieg, A., A. M. Huger, G. A. Langenbruch, W. Schnetter (1983) *Z. ang. Ent.* 96:500–508.

Lereclus, D. et al. (1989) *FEMS Microbiology Letters* 60:211–218.

Maniatis, T., E. F. Fritsch, J. Sambrook (1982) *Molecular Cloning: A Laboratory Manual*, Cold Spring Harbor Laboratory, Cold Spring Harbor, N.Y.

Martens, J. W. M., G. Honee, D. Zuidema, J. W. M. van Lent, B. Visser, J. M. Vlak (1990) *Appl. Environmental Microbiol.* 56(9):2764–2770.

Merryweather, A. T., U. Weyer, M. P. G. Harris, M. Hirst, T. Booth, R. D. Possee (1990) *J. Gen. Virol.* 71:1535–1544.

Prefontaine, G., P. Fast, P. C. K. Lau, M. A. Hefford, Z. Hanna, R. Brosseau (1987) *Appl. Environ. Microbiol.* 53(12):2808–2814.

Prichard, R. K. et al. (1980) "The problem of anthelmintic resistance in nematodes," *Austr. Vet. J.* 56:239–251.

Sanger et al. [1977] *Proc. Natl. Acad. Sci. USA* 74:5463–5467.

Schnepf, H. E., H. R. Whiteley (1981) *Proc. Natl. Acad. Sci. USA* 78:2893–2897.

We claim:

1. A polynucleotide sequence from a *Bacillus thuringiensis* isolate selected from the group consisting of PS80JJ1, PS158D5, PS167P, PS169E, PS177F1, PS177G, PS204G4, and PS204G6, which encodes a toxin active against nematodes.

2. The polynucleotide sequence, according to claim 1, which encodes a toxin of SEQ ID NO. 4.

3. The polynucleotide sequence, according to claim 2, which is shown in SEQ ID NO. 3.

4. The polynucleotide sequence, according to claim 1, which encodes a toxin of SEQ ID NO. 6.

5. The polynucleotide sequence, according to claim 4, which is shown in SEQ ID NO. 5.

6. A polynucleotide sequence which encodes a protein toxic to nematodes, wherein said polynucleotide sequence that can be amplified using SEQ ID NO. 1 and SEQ ID NO. 2 as primers.

7. The polynucleotide sequence, according to claim 6, which encodes a toxin selected from the group consisting of SEQ ID NO. 4 and SEQ ID NO. 6.

8. The polynucleotide sequence, according to claim 7, which comprises a polynucleotide sequence selected from the group consisting of SEQ ID NO. 3 and SEQ ID NO. 5.

* * * * *

UNITED STATES PATENT AND TRADEMARK OFFICE
CERTIFICATE OF CORRECTION

PATENT NO. : 5,589,382

DATED : December 31, 1996

INVENTOR(S) : Jewel Payne, Kenneth Narva, Jenny Fu

It is certified that error appears in the above-identified patent and that said Letters Patent is hereby corrected as shown below:

Column 1: Line 62: "CryII" should read --CryII--.
Column 1: Line 63: "CryIII" should read --CryIII--.
Column 13: Line 36: "HindIII" should read --HindIII--.
Column 36: Lines 40-41: Claim 6: "sequence that can be amplified" should read
  --sequence can be amplified--.

Signed and Sealed this

Sixth Day of May, 1997

Attest:

BRUCE LEHMAN

Attesting Officer  Commissioner of Patents and Trademarks